United States Patent
Meyer et al.

(10) Patent No.: US 9,889,078 B2
(45) Date of Patent: *Feb. 13, 2018

(54) SKIN AND/OR HAIR WHITENING MIXTURE

(71) Applicant: Symrise AG, Holzminden (DE)

(72) Inventors: Imke Meyer, Bodenwerder (DE); Gabriele Vielhaber, Paris (FR); Aurélie Trunet, Levallois Perret (FR); Mareille Le Maire, Boulogne-Billancourt (FR)

(73) Assignee: Symrise AG, Holzminden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/471,529

(22) Filed: Aug. 28, 2014

(65) Prior Publication Data

US 2015/0064122 A1 Mar. 5, 2015

(30) Foreign Application Priority Data

Sep. 2, 2013 (EP) .................................... 13182603

(51) Int. Cl.

| | | |
|---|---|---|
| *A61Q 5/08* | (2006.01) | |
| *A61Q 15/00* | (2006.01) | |
| *A61Q 17/04* | (2006.01) | |
| *A61Q 19/00* | (2006.01) | |
| *A61Q 19/08* | (2006.01) | |
| *A61K 8/34* | (2006.01) | |
| *A61Q 19/02* | (2006.01) | |
| *A61Q 19/10* | (2006.01) | |

(52) U.S. Cl.
CPC ................ *A61K 8/347* (2013.01); *A61K 8/34* (2013.01); *A61K 8/345* (2013.01); *A61Q 5/08* (2013.01); *A61Q 19/02* (2013.01); *A61K 2800/592* (2013.01); *A61Q 15/00* (2013.01); *A61Q 17/04* (2013.01); *A61Q 19/00* (2013.01); *A61Q 19/08* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 2009/0148391 A1* | 6/2009 | Schmaus ................ | A61K 8/347 424/59 |
| 2009/0263513 A1* | 10/2009 | Marini .................... | A61K 8/347 424/729 |
| 2010/0104524 A1* | 4/2010 | Lee ........................ | A61K 8/4973 424/62 |
| 2011/0171288 A1* | 7/2011 | Mohammadi ........ | A61K 8/0295 424/450 |

FOREIGN PATENT DOCUMENTS

| | | |
|---|---|---|
| EP | 1 847 247 A1 | 10/2007 |
| WO | 03/049713 A1 | 6/2003 |
| WO | 2007/077258 A1 | 7/2007 |
| WO | 2007/077260 A1 | 7/2007 |
| WO | 2008/105632 A1 | 9/2008 |

* cited by examiner

*Primary Examiner* — Jyothsna Venkat
(74) *Attorney, Agent, or Firm* — Dilworth & Barrese, LLP

(57) ABSTRACT

Suggested is a skin or hair whitening mixture, comprising (a) resorcinol derivatives of formula (I)

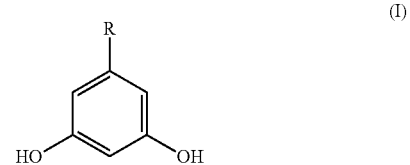

(I)

in which R stands for an alkyl radical having 3 to 10 carbon atoms or an optionally substituted alkylphenyl radical having 8 to 16 carbon atoms, and
(b) bisabolol, and optionally
(c) alkandiols having 3 to 10 carbon atoms.

6 Claims, No Drawings

SKIN AND/OR HAIR WHITENING MIXTURE

FIELD OF INVENTION

The present invention relates to the area of cosmetics and refers to a synergistic mixture of actives for whitening of skin and hair.

STATE OF THE ART

Skin whitening has a long history in Asia, stemming back to ancient China. A white complexion was seen as noble and aristocratic, especially in southern parts of China and Asia, where the sun was always out. That trend for a white complexion continued until today. Due to the fact that the majority of women are concerned over skin darkening, whitening products are the key segment of the skin care market in China. It makes up nearly 30% of the total skin care market in China. Chinese consumers are big users of facial whitening products with facial care accounting for over 80%.

Consumers outside of Asia are also concerned about skin darkening and complexion issues. For instance people of dark skin types are particularly affected by facial hyper-pigmentation and more and more consumers feel uncomfortable with their axillary zone being also subject to darkening. Caucasian women whereas are more concerned about dark spots and freckles on face and hands.

Nowadays, the whitening market has come a long way from the basic 'whitening' approach, aimed at ethnic consumers with darker skin mainly in Asia or the Middle East to new rising targets driven by the aging of the population and men's increasing interest in grooming. Consumers are globally concerned about sun aging and are looking for products to protect their skin to avoid premature age spots or wrinkles.

Another problem is associated with the fact that following repetitive shaving and depilatory treatments the armpit area often becomes darker with a loss of evenness due Post Inflammatory Hyper-pigmentation (PIH) and skin thickening. Inflammation may result in hyper-pigmentation through several mechanisms like the direct stimulation of melanocytes by inflammatory mediators such as IL-1-alpha and TNF-alpha. Reactive Oxygen Species (ROS) are also known stimulators of melanocytes.

To meet the global increasing need for modern, safe and effective skin lightening ingredients the challenge is on the raw material suppliers' side. Many common skin lightening ingredients in the cosmetic market are reported to be unsafe, cytotoxic, unstable or ineffective at low concentrations. The most common lightening ingredients today are the tyrosinase inhibitors kojic acid and arbutin as well as ascorbic acid derivatives. However, all these compounds exhibit significant disadvantages: kojic acid has been shown to be sensitizing and to exhibit adverse thyroid effects at high concentrations. Arbutin is suspected to be a hydroquinone precursor. Hydroquinone is known for its toxic action on skin cells and therefore its cosmetic use has been restricted or banned in many countries. Ascorbic acid derivatives are only effective in high concentrations and difficult to stabilize in cosmetic formulations.

Therefore, the object underlying the present invention has been to provide an active mixture that is not only more effective in whitening skin and hair when compared with standard products like kojic acid or arbutin, but is simultaneously dermatological safe, stable even at higher temperatures and easy to formulate into cosmetic compositions.

Another object of the invention has been to provide a skin and hair whitening active mixture that has anti-oxidative power, is able to scavenge free radicals and to reduce inflammatory response and stimulation of melanocytes. Finally, the mixtures need to be potent IL-1-alpha and TNF-alpha-inhibitors, able to reduce the inflammatory response that leads to hyper-pigmentation and to exhibit an anti-irritant effect for immediate skin relief.

DESCRIPTION OF THE INVENTION

Object of the present invention is a skin and hair whitening mixture, comprising
(a) resorcinol derivatives of formula (I)

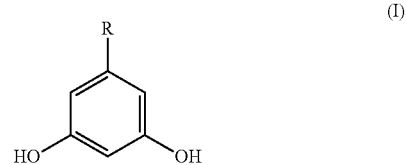

(I)

in which R stands for an alkyl radical having 3 to 10 carbon atoms or an optionally substituted alkylphenyl radical having 8 to 16 carbon atoms, and
(b) bisabolol, and optionally
(c) alkandiols having 3 to 10 carbon atoms.

Surprisingly, it has been observed that the mixtures according to the present invention fully comply with the complex profile explained above. Particularly, the mixture significantly decreases the melanin content of skin and hair, lightens the skin tone, treats uneven skin tones, reduces dark spots, and shows skin brightening efficacy and reduction of appearance of dark hair. It is also a powerful anti-oxidant, scavenging free radicals and reducing inflammatory response and stimulation of melanocytes. The mixtures are potent IL-1-alpha and TNF-alpha-inhibitors, able to reduce the inflammatory response that leads to hyperpigmentation. Another advantage is that the products exhibit an anti-irritant effect for immediate skin relief. The mixture is oil soluble, easy to formulate, and below a pH of 8 stable up to 80° C. Finally, all ingredients are China compliant (SFDA approved).

Resorcinol Derivatives

Resorcinol derivatives of formula (I) which are forming group (a) represent well known compounds that can be obtained in the market. Preferably, the compounds are selected from the group consisting of butyl resorcinol, pentyl resorcinol, hexyl resorcinol, heptyl resorcinol, octyl resorcinol, nonyl resorcinol, decylresorcinol, phenylethyl resorcinol, phenylpropyl resorcinol, phenylbutyl resorcinol, phenylhexyl resorcinol, toluoylethyl resorcinol, toluoylpropyl resorcinol, toluoylbutyl resorcinol, toluoylhexyl resorcinol, methoxytoluoylethyl resorcinol, methoxytoluoylpropyl resorcinol, methoxytoluoylbutyl resorcinol, methoxyltoluoylhexyl resorcinol, dimethoxytoluoylethyl resorcinol, dimethoxytoluoylpropyl resorcinol, dimethoxytoluoylbutyl resorcinol, dimethoxytoluoylhexyl resorcinol and their mixtures. The preferred structures are hexyl resorcinol, dimethoxytoluoylhexyl resorcinol and in particular Phenylethyl resorcinol.

Bisabolol

Bisabolol (component b) or more formally α-(−)-bisabolol or also known as levomenol, is a natural monocyclic sesquiterpene alcohol. It is a colorless viscous oil that is the primary constituent of the essential oil from German chamomile (*Matricaria recutita*) and *Myoporum crassifolium*. It is almost insoluble in water and glycerin, but well soluble in ethanol. The enantiomer, α-(+)-bisabolol, is also found naturally but is rare. Synthetic bisabolol is usually a racemic mixture of the two, α-(±)-bisabolol.

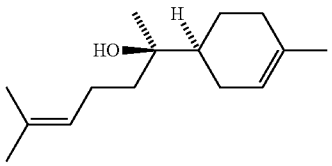 [SMILES: CC(C)=CCC[C@@](C)(O)[C@@H]1CC=C(C)CC1]

Bisabolol has a weak sweet floral aroma and is used in various fragrances. It has also been used for hundreds of years in cosmetics because of its perceived skin healing properties. Bisabolol is known to have anti-irritant, anti-inflammatory and anti-microbial properties. Bisabolol is also demonstrated to enhance the percutaneous absorption of certain molecules. Bisabolol has not been reported to enhance the whitening power of actives like the resorcinol derivatives forming group (a).

Alkandiols

Alkandiols forming group (c) do not show any whitening activity, but improve bioavailability of the other actives and boost the performance of the composition significantly. The preferred structures are selected from the group consisting of 1,2-propandiol, 1,3-propandiol, 1,2-butandiol, 1,2-pentandiol, 1,2-hexandiol, 1,2-heptandiol, 1,2-octandiol, 1,2-nonandiol, 1,2-decandiol and their mixtures.

An overall preferred mixture comprises phenylethyl resorcinol, bisabolol and 1,2-pentandiol.

Mixtures

In another preferred embodiment of the invention the components are present in the following amounts:
(a) about 30 to about 99% b.w., preferably about 40 to about 80% b.w. resorcinol derivatives of formula (I),
(b) about 1 to about 20% b.w., preferably about 5 to about 10% b.w. bisabolol, and
(c) 0 to about 60% b.w., preferably about 10 to about 50% b.w., and more preferably about 15 to about 40% b.w. alkandiols,
on condition that the amounts add to 100% b.w.

The mixtures may be solved in a cosmetically acceptable oil body. Suitable oil bodies encompass for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular dioctyl malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

Such composition may comprise about 1 to about 40% b.w, preferably 5 to about 30% b.w. and more preferably about 10 to about 20% b.w. of the mixture (a+b+c) and to 100% b.w. at least one oil body, preferably a neutral oil such as for example caprylic/capric triglycerides.

Cosmetic Compositions

Another object of the present invention is directed to a cosmetic composition comprising the mixture comprising the components (a), (b) and optionally (c) in the reported amounts. Said mixtures may be present in said cosmetic compositions in an amount of from about 0.1 to about 10% b.w., preferably about 0.05 to about 5% b.w. and more preferably about 0.5 to about 1.5% b.w.—calculated on the composition.

Said compositions may be formulated as an anti-ageing face cream, a BB cream, an anti-dark spot cream, a whitening post depilatory cream, a whitening deodorant, a body lotion or a soap and body wash.

The compositions according to the invention may contain abrasives, anti-acne agents, agents against ageing of the skin, anti-cellulitis agents, antidandruff agents, anti-inflammatory agents, irritation-preventing agents, irritation-inhibiting agents, antioxidants, astringents, perspiration-inhibiting agents, antiseptic agents, anti-statics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, skin-soothing agents, skin-cleansing agents, skin care agents, skin-healing agents, skin-lightening agents, skin-protecting agents, skin-softening agents, hair promotion agents, cooling agents, skin-cooling agents, warming agents, skin-warming agents, stabilizers, UV-absorbing agents, UV filters, detergents, fabric conditioning agents, suspending agents, skin-tanning agents, thickeners, vitamins, oils, waxes, fats, phospholipids, saturated fatty acids, mono- or polyunsaturated fatty acids, α-hydroxy acids, polyhydroxyfatty acids, liquefiers, dyestuffs, colour-protecting agents, pigments, anti-corrosives, aromas, flavouring substances, odoriferous substances, polyols, surfactants, electrolytes, organic solvents or silicone derivatives and the like as additional auxiliaries and additives.

Among these auxiliaries additional skin and hair whitening (or modulating) agents (optional component d) and primary and/or secondary sun protection factors (optional component e) are particularly preferred.

A.1 Surfactants

Other preferred auxiliaries and additives are anionic and/or amphoteric or zwitterionic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. The percentage content of surfactants in the preparations may be from 0.1 to 10% by weight and is preferably from 0.5 to 5% by weight, based on the preparation.

A.2 Oil Bodies

Suitable oil bodies, which form constituents of the 0/W emulsions, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

A.3 Emulsifiers

Other surfactants may also be added to the preparations as emulsifiers, including for example:
  products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;
  $C_{12/18}$ fatty acid monoesters and diesters of addition products of 1 to 30 mol ethylene oxide onto glycerol;
  glycerol mono- and diesters and sorbitan mono- and diesters of saturated and unsaturated fatty acids containing 6 to 22 carbon atoms and ethylene oxide addition products thereof;
  addition products of 15 to 60 mol ethylene oxide onto castor oil and/or hydrogenated castor oil;
  polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;
  addition products of 2 to 15 mol ethylene oxide onto castor oil and/or hydrogenated castor oil;
  partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);
  mono-, di and trialkyl phosphates and mono-, di- and/or tri-PEG-alkyl phosphates and salts thereof;
  wool wax alcohols;
  polysiloxane/polyalkyl polyether copolymers and corresponding derivatives;
  mixed esters of pentaerythritol, fatty acids, citric acid and fatty alcohol and/or mixed esters of $C_{6-22}$ fatty acids, methyl glucose and polyols, preferably glycerol or polyglycerol,
  polyalkylene glycols and
  glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

(i) Partial glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

(ii) Sorbitan esters. Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

(iii) Polyglycerol esters. Typical examples of suitable polyglycerol esters are Polyglyceryl-2 Dipolyhydroxystearate (Dehymuls PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyolesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

(iv) Anionic emulsifiers. Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

(v) Amphoteric emulsifiers. Other suitable emulsifiers are amphoteric or zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

A.4 Superfatting Agents and Consistency Factors

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

A.5 Thickening Agents and Rheology Additives

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

A.6 Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol and the various polyquaternium types (for example 6, 7, 32 or 37) which can be found in the market under the tradenames Rheocare® CC or Ultragel® 300.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

A.7 Pearlising Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

A.8 Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in *Cosm. Toil.* 91, 27 (1976).

A.9 Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes. Metal salts of fatty acids such as, for example, magnesium, aluminium and/or zinc stearate or ricinoleate may be used as stabilizers.

A.10 Primary Sun Protection Factors

Primary sun protection factors in the context of the invention are, for example, organic substances (light filters) which are liquid or crystalline at room temperature and which are capable of absorbing ultraviolet radiation and of releasing the energy absorbed in the form of longer-wave radiation, for example heat.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

Preferred cosmetic compositions, preferably topical formulations according to the present invention comprise one, two, three or more sun protection factors selected from the group consisting of 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivatives and indole derivatives.

In addition, it is advantageous to combine compounds of formula (I) with active ingredients which penetrate into the skin and protect the skin cells from inside against sunlight-induced damage and reduce the level of cutaneous matrix metalloproteases. Preferred respective ingredients, so called arylhydrocarbon receptor antagonists, are described in WO 2007/128723, incorporated herein by reference. Preferred is 2-benzylidene-5,6-dimethoxy-3,3-dimethylindan-1-one.

The UV filters cited below which can be used within the context of the present invention are preferred but naturally are not limiting.

UV filters which are preferably used are selected from the group consisting of
p-aminobenzoic acid
p-aminobenzoic acid ethyl ester (25 mol) ethoxylated (INCI name: PEG-25 PABA)
p-dimethylaminobenzoic acid-2-ethylhexyl ester
p-aminobenzoic acid ethyl ester (2 mol) N-propoxylated
p-aminobenzoic acid glycerol ester
salicylic acid homomethyl ester (homosalates) (Neo Heliopan® HMS)
salicylic acid-2-ethylhexyl ester (Neo Heliopan® OS)
triethanolamine salicylate
4-isopropyl benzyl salicylate
anthranilic acid menthyl ester (Neo Heliopan® MA)
diisopropyl cinnamic acid ethyl ester
p-methoxycinnamic acid-2-ethylhexyl ester (Neo Heliopan® AV)
diisopropyl cinnamic acid methyl ester
p-methoxycinnamic acid isoamyl ester (Neo Heliopan® E 1000)
p-methoxycinnamic acid diethanolamine salt
p-methoxycinnamic acid isopropyl ester 2-phenylbenzimidazole sulfonic acid and salts (Neo Heliopan® Hydro)
3-(4'-trimethylammonium) benzylidene bornan-2-one methyl sulfate
beta-imidazole-4(5)-acrylic acid (urocanic acid)
3-(4'-sulfo)benzylidene bornan-2-one and salts
3-(4'-methyl benzylidene)-D,L-camphor (Neo Heliopan® MBC)
3-benzylidene-D,L-camphor
N-[(2 and 4)-[2-(oxoborn-3-ylidene) methyl]benzyl]acrylamide polymer
4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb® HEB)
benzylidene malonate polysiloxane (Parsol® SLX)
glyceryl ethylhexanoate dimethoxycinnamate
dipropylene glycol salicylate
tris(2-ethylhexyl)-4,4',4''-(1,3,5-triazine-2,4,6-triyltriimino)tribenzoate(=2,4,6-trianilino(p-carbo-2'-ethylhexyl-1'-oxy)-1,3,5-triazine) (Uvinul® T150)

Broadband filters which are preferably combined with one or more compounds of formula (I) in a preparation according to the present invention are selected from the group consisting of
2-ethylhexyl-2-cyano-3,3-diphenyl acrylate (Neo Heliopan®303)
ethyl-2-cyano-3,3'-diphenyl acrylate
2-hydroxy-4-methoxybenzophenone (Neo Heliopan® BB)
2-hydroxy-4-methoxybenzophenone-5-sulfonic acid
dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octoxybenzophenone
2-hydroxy-4-methoxy-4'-methyl benzophenone
sodium hydroxymethoxybenzophenone sulfonate
disodium-2,2'-dihydroxy-4,4'-dimethoxy-5,5'-disulfobenzophenone
phenol, 2-(2H-benzotriazol-2-yl)-4-methyl-6-(2-methyl-3 (1,3,3,3-tetramethyl-1-(trimethylsilyl)oxy)disiloxanyl) propyl) (Mexoryl® XL)
2,2'-methylene bis-(6-(2H-benzotriazol-2-yl)-4-1,1,3,3-tetramethylbutyl)phenol) (Tinosorb® M)
2,4-bis-[4-(2-ethylhexyloxy)-2-hydroxyphenyl]-1,3,5-triazine
2,4-bis-[{(4-(2-ethylhexyloxy)-2-hydroxy}phenyl]-6-(4-methoxyphenyl)-1,3,5-triazine (Tinosorb® S)
2,4-bis-[{(4-(3-sulfonato)-2-hydroxypropyloxy)-2-hydroxy}phenyl]-6-(4-methoxyphenyl)-1,3,5-triazine sodium salt
2,4-bis-[{(3-(2-propyloxy)-2-hydroxypropyloxy)-2-hydroxyl}phenyl]-6-(4-methoxyphenyl)-1,3,5-triazine
2,4-bis-[{4-(2-ethylhexyloxy)-2-hydroxy}phenyl]-6-[4-(2-methoxyethylcarbonyl) phenylamino]-1,3,5-triazine
2,4-bis-[{4-(3-(2-propyloxy)-2-hydroxypropyloxy)-2-hydroxyl}phenyl]-6-[4-(2-ethylcarboxyl) phenylamino]-1,3,5-triazine
2,4-bis-[{4-(2-ethylhexyloxy)-2-hydroxy}phenyl]-6-(1-methylpyrrol-2-yl)-1,3,5-triazine
2,4-bis-[{4-tris-(trimethylsiloxysilylpropyloxy)-2-hydroxy}phenyl]-6-(4-methoxyphenyl)-1,3,5-triazine
2,4-bis-[{4-(2''-methylpropenyloxy)-2-hydroxy}phenyl]-6-(4-methoxyphenyl)-1,3,5-triazine
2,4-bis-[{4-(1',1',1',3',5',5',5'-heptamethylsiloxy-2''-methylpropyloxy)-2-hydroxyl}phenyl]-6-(4-methoxyphenyl)-1,3,5-triazine UV-A filters filters which are preferably combined with one or more compounds of formula (I) in a preparation according to the present invention are selected from the group consisting of
4-isopropyl dibenzoyl methane
terephthalylidene dibornane sulfonic acid and salts (Mexoryl® SX)
4-t-butyl-4'-methoxydibenzoyl methane (avobenzone)/ (Neo Heliopan® 357)
phenylene bis-benzimidazyl tetrasulfonic acid disodium salt (Neo Heliopan® AP)
2,2'-(1,4-phenylene)-bis-(1H-benzimidazole-4,6-disulfonic acid), monosodium salt
2-(4-diethylamino-2-hydroxybenzoyl) benzoic acid hexyl ester (Uvinul® A Plus)
indanylidene compounds in accordance with DE 100 55 940 A1 (=WO 2002 038537 A1)

UV filters which are more preferably combined with one or more compounds of formula (I) in a preparation according to the present invention are selected from the group consisting of
p-aminobenzoic acid
3-(4'-trimethylammonium) benzylidene bornan-2-one methyl sulfate
salicylic acid homomethyl ester (Neo Heliopan® HMS)
2-hydroxy-4-methoxybenzophenone (Neo Heliopan® BB)
2-phenylbenzimidazole sulfonic acid (Neo Heliopan® Hydro)
terephthalylidene dibornane sulfonic acid and salts (Mexoryl® SX)
4-tert-butyl-4'-methoxydibenzoyl methane (Neo Heliopan® 357)
3-(4'-sulfo)benzylidene bornan-2-one and salts
2-ethylhexyl-2-cyano-3,3-diphenyl acrylate (Neo Heliopan® 303)
N-[(2 and 4)-[2-(oxoborn-3-ylidene) methyl]benzyl]acrylamide polymer
p-methoxycinnamic acid-2-ethylhexyl ester (Neo Heliopan® AV)
p-aminobenzoic acid ethyl ester (25 mol) ethoxylated (INCI name: PEG-25 PABA)
p-methoxycinnamic acid isoamyl ester (Neo Heliopan®E1000)
2,4,6-trianilino-(p-carbo-2'-ethylhexyl-1'-oxy)-1,3,5-triazine (Uvinul® T150)
phenol, 2-(2H-benzotriazol-2-yl)-4-methyl-6-(2-methyl-3 (1,3,3,3-tetramethyl-1-(trimethylsilyl)oxy)disiloxanyl) propyl) (Mexoryl® XL)
4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb HEB)
3-(4'-methyl benzylidene)-D,L-camphor (Neo Heliopan® MBC)
3-benzylidene camphor
salicylic acid-2-ethylhexyl ester (Neo Heliopan® OS)
4-dimethylaminobenzoic acid-2-ethylhexyl ester (Padimate O)
hydroxy-4-methoxybenzophenone-5-sulfonic acid and Na salt
2,2'-methylene bis-(6-(2H-benzotriazol-2-yl)-4-1,1,3,3-tetramethylbutyl) phenol) (Tinosorb® M)
phenylene bis-benzimidazyl tetrasulfonic acid disodium salt (Neo Heliopan® AP)
2,4-bis-[{(4-(2-ethylhexyloxy)-2-hydroxy}phenyl]-6-(4-methoxyphenyl)-1,3,5-triazine (Tinosorb® S)
benzylidene malonate polysiloxane (Parsol® SLX)

menthyl anthranilate (Neo Heliopan® MA)
2-(4-diethylamino-2-hydroxybenzoyl) benzoic acid hexyl ester (Uvinul® A Plus)
indanylidene compounds in accordance with DE 100 55 940 (=WO 02/38537).

Advantageous primary and also secondary sun protection factors are mentioned in WO 2005 123101 A1. Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment a formulation according to the invention contains a total amount of sunscreen agents, i.e. in particular UV filters and/or inorganic pigments (UV filtering pigments) so that the formulation according to the invention has a light protection factor of greater than or equal to 2 (preferably greater than or equal to 5). Such formulations according to the invention are particularly suitable for protecting the skin and hair.

A.11 Secondary Sun Protection Factors

Besides the groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages, also (metal) chelators (for example alpha-hydroxyfatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Advantageous inorganic secondary light protection pigments are finely dispersed metal oxides and metal salts which are also mentioned in WO 2005 123101 A1. The total quantity of inorganic pigments, in particular hydrophobic inorganic micro-pigments in the finished cosmetic preparation according to the present invention is advantageously from 0.1 to 30% by weight, preferably 0.5 to 10.0% by weight, in each case based on the total weight of the preparation.

Also preferred are particulate UV filters or inorganic pigments, which can optionally be hydrophobed, can be used, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures thereof.

A.12 Actives Modulating Skin and/or Hair Pigmentation

Preferred active ingredients for skin and/or hair lightening are selected from the group consisting of:
kojic acid (5-hydroxy-2-hydroxymethyl-4-pyranone), kojic acid derivatives, preferably kojic acid dipalmitate, arbutin, ascorbic acid, ascorbic acid derivatives, preferably magnesium ascorbyl phosphate, hydroquinone, hydroquinone derivatives, resorcinol, cyclohexylcarbamates (preferably one or more cyclohexyl carbamates disclosed in WO 2010/122178 and WO 2010/097480), sulfur-containing molecules, preferably glutathione or cysteine, alpha-hydroxy acids (preferably citric acid, lactic acid, malic acid), salts and esters thereof, N-acetyl tyrosine and derivatives, undecenoyl phenylalanine, gluconic acid, chromone derivatives, preferably aloesin, flavonoids, 1-aminoethyl phosphinic acid, thiourea derivatives, ellagic acid, nicotinamide (niacinamide), zinc salts, preferably zinc chloride or zinc gluconate, thujaplicin and derivatives, triterpenes, preferably maslinic acid, sterols, preferably ergosterol, benzofuranones, preferably senkyunolide, vinyl guiacol, ethyl guiacol, dionic acids, preferably octodecene dionic acid and/or azelaic acid, inhibitors of nitrogen oxide synthesis, preferably L-nitroarginine and derivatives thereof, 2,7-dinitroindazole or thiocitrulline, metal chelators (preferably alpha-hydroxy fatty acids, phytic acid, humic acid, bile acid, bile extracts, EDTA, EGTA and derivatives thereof), retinoids, soy milk and extract, serine protease inhibitors or lipoic acid or other synthetic or natural active ingredients for skin and hair lightening, the latter preferably used in the form of an extract from plants, preferably bearberry extract, rice extract, papaya extract, turmeric extract, mulberry extract, bengkoang extract, nutgrass extract, liquorice root extract or constituents concentrated or isolated therefrom, preferably glabridin or licochalcone A, artocarpus extract, extract of *rumex* and *ramulus* species, extracts of pine species (pinus), extracts of *vitis* species or stilbene derivatives isolated or concentrated therefrom, saxifrage extract, scutelleria extract, grape extract and/or microalgae extract, in particular *Tetraselmis suecica* Extract.

Preferred additional skin lighteners are kojic acid as tyrosinase inhibitor, beta- and alphaarbutin, hydroquinone, nicotinamide, dioic acid, Mg ascorbyl phosphate and vitamin C and its derivatives, mulberry extract, Bengkoang extract, papaya extract, turmeric extract, nutgrass extract, licorice extract (containing glycyrrhizin), alpha-hydroxyacids, 4-alkylresorcinols, 4-hydroxyanisole. These skin lighteners are preferred due to their very good activity, in particular in combination with sclareolide according to the present invention. In addition, said preferred skin lighteners are readily available.

Advantageous skin and hair tanning active ingredients in this respect are substrates or substrate analogues of tyrosinase such as L-tyrosine, N-acetyl tyrosine, L-DOPA or L-dihydroxyphenylalanine, xanthine alkaloids such as caffeine, theobromine and theophylline and derivatives thereof, proopiomelanocortin peptides such as ACTH, alpha-MSH, peptide analogues thereof and other substances which bind to the melanocortin receptor, peptides such as Val-Gly-Val-Ala-Pro-Gly, Lys-Ile-Gly-Arg-Lys or Leu-Ile-Gly-Lys, purines, pyrimidines, folic acid, copper salts such as copper gluconate, chloride or pyrrolidonate, 1,3,4-oxadiazole-2-thiols such as 5-pyrazin-2-yl-1,3,4-oxadiazole-2-thiol, curcumin, zinc diglycinate (Zn(Gly)2), manganese(II) bicarbonate complexes ("pseudocat-alases") as described for example in EP 0 584 178, tetrasubstituted cyclohexene derivatives as described for example in WO 2005/032501, isoprenoids as described in WO 2005/102252 and in WO 2006/010661, melanin derivatives such as Melasyn-100 and MelanZe, diacyl glycerols, aliphatic or cyclic diols, psoralens, prostaglandins and analogues thereof, activators of adenylate cyclase and compounds which activate the transfer of melanosomes to keratinocytes such as serine proteases or agonists of the PAR-2 receptor, extracts of plants and plant parts of the chrysanthemum species, *sanguisorba* species, walnut extracts, urucum extracts, rhubarb extracts, microalgae extracts, in particular *Isochrysis galbana*, trehalose, erythru-lose and dihydroxyacetone. Flavonoids which bring about skin and hair tinting or browning (e.g. quercetin, rhamnetin, kaempferol, fisetin, genistein, daidzein, chrysin and api-genin, epicatechin, diosmin and diosmetin, morin, quercitrin, naringenin, hesperidin, phloridzin and phloretin) can also be used.

The amount of the aforementioned examples of additional active ingredients for the modulation of skin and hair pigmentation (one or more compounds) in the products according to the invention is then preferably 0.00001 to 30 wt. %, preferably 0.0001 to 20 wt. %, particularly preferably 0.001 to 5 wt. %, based on the total weight of the preparation.

A.13 Anti-Ageing Actives

In the context of the invention, anti-ageing or biogenic agents are, for example antioxidants, matrix-metalloproteinase inhibitors (MMPI), skin moisturizing agents, glycosaminglycan stimulkators, anti-inflammatory agents, TRPV1 antagonists and plant extracts.

(i) Antioxidants. Suitable antioxidants encompass amino acids (preferably glycine, histidine, tyrosine, tryptophane) and derivatives thereof, imidazoles (preferably urocanic acid) and derivatives thereof, peptides, preferably D,L-carnosine, D-carnosine, L-carnosine and derivatives thereof (preferably anserine), carnitine, creatine, matrikine peptides (preferably lysyl-threonyl-threonyl-lysyl-serine) and palmitoylated pentapeptides, carotenoids, carotenes (preferably alpha-carotene, beta-carotene, lycopene) and derivatives thereof, lipoic acid and derivatives thereof (preferably dihydrolipoic acid), aurothioglucose, propyl thiouracil and other thiols (preferably thioredoxine, glutathione, cysteine, cystine, cystamine and glycosyl, N-acetyl, methyl, ethyl, propyl, amyl, butyl and lauryl, palmitoyl, oleyl, gamma-linoleyl, cholesteryl, glyceryl and oligoglyceryl esters thereof) and salts thereof, dilauryl thiodipropionate, distearyl thiodipropionate, thiodipropionic acid and derivatives thereof (preferably esters, ethers, peptides, lipids, nucleotides, nucleosides and salts) and sulfoximine compounds (preferably buthionine sulfoximines, homocysteine sulfoximine, buthionine sulfones, penta-, hexa-, heptathionine sulfoximine) in very small tolerated doses (e.g. pmol to µmol/kg), also (metal) chelators (preferably alpha-hydroxy fatty acids, palmitic acid, phytic acid, lactoferrin, alpha-hydroxy acids (preferably citric acid, lactic acid, malic acid), humic acid, bile acid, bile extracts, tannins, bilirubin, biliverdin, EDTA, EGTA and derivatives thereof), unsaturated fatty acids and derivatives thereof (preferably gamma-linolenic acid, linoleic acid, oleic acid), folic acid and derivatives thereof, ubiquinone and derivatives thereof, ubiquinol and derivatives thereof, vitamin C and derivatives (preferably ascorbyl palmitate, Mg ascorbyl phosphate, ascorbyl acetate, ascorbyl glucoside), tocopherols and derivatives (preferably vitamin E acetate), vitamin A and derivatives (vitamin A palmitate) and coniferyl benzoate of benzoic resin, rutinic acid and derivatives thereof, flavonoids and glycosylated precursors thereof, in particular quercetin and derivatives thereof, preferably alpha-glucosyl rutin, rosmarinic acid, carnosol, carnosolic acid, resveratrol, caffeic acid and derivatives thereof, sinapic acid and derivatives thereof, ferulic acid and derivatives thereof, curcuminoids, chlorogenic acid and derivatives thereof, retinoids, preferably retinyl palmitate, retinol or tretinoin, ursolic acid, levulinic acid, butyl hydroxytoluene, butyl hydroxyanisole, nordihydroguaiac acid, nordihydroguaiaretic acid, trihydroxybutyrophenone, uric acid and derivatives thereof, mannose and derivatives thereof, zinc and derivatives thereof (preferably ZnO, $ZnSO_4$), selenium and derivatives thereof (preferably selenium methionine), superoxide dismutase, stilbenes and derivatives thereof (preferably stilbene oxide, trans-stilbene oxide) and the derivatives (salts, esters, ethers, sugars, nucleotides, nucleosides, peptides and lipids) of these cited active ingredients which are suitable according to the invention or extracts or fractions of plants having an antioxidant effect, preferably green tea, rooibos, honeybush, grape, rosemary, sage, melissa, thyme, lavender, olive, oats, cocoa, ginkgo, ginseng, liquorice, honeysuckle, *sophora*, pueraria, pinus, citrus, Phyllanthus emblica or St. John's wort, grape seeds, wheat germ, Phyllanthus emblica, coenzymes, preferably coenzyme Q10, plastoquinone and menaquinone. Preferred antioxidants are selected from the group consisting of vitamin A and derivatives, vitamin C and derivatives, tocopherol and derivatives, preferably tocopheryl acetate, and ubiquinone.

If vitamin E and/or derivatives thereof are used as the antioxidant(s), it is advantageous to choose their concentrations from the range from about 0.001 to about 10% b.w. based on the total weight of the formulation. If vitamin A or vitamin A derivatives or carotenes or derivatives thereof are used as the antioxidant(s), it is advantageous to choose their concentrations from the range from about 0.001 to about 10% b.w. based on the total weight of the formulation.

(ii) Matrix-Metalloproteinase inhibitors (MMPI). Preferred compositions comprise matrix-metalloproteinase inhibitors, especially those inhibiting matrix-metalloproteinases enzymatically cleaving collagen, selected from the group consisting of: ursolic acid, retinyl palmitate, propyl gallate, precocenes, 6-hydroxy-7-methoxy-2,2-dimethyl-1 (2H)benzopyran, 3,4-dihydro-6-hydroxy-7-methoxy-2,2- dimethyl-1(2H)-benzopyran, benzamidine hydrochloride, the cysteine proteinase inhibitors N-ethylmalemide and epsilon-amino-n-caproic acid of the serinprotease inhibitors: phenylmethylsulfonylfluoride, collhibin (company Pentapharm; INCI: hydrolysed rice protein), oenotherol (company Soliance; INCI: propylene glycol, aqua, Oenothera biennis root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and *lentinus edodes* extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and further plant extracts, which are listed in WO 02 069992 A1 (see tables 1-12 there, incorporated herein by reference), proteins or glycoproteins from soya, hydrolysed proteins from rice, pea or lupine, plant extracts which inhibit MMPs, preferably extracts from shitake mushrooms, extracts from the leaves of the Rosaceae family, sub-family Rosoideae, quite particularly extracts of blackberry leaf (preferably as described in WO 2005 123101 A1, incorporated herein by reference) as e.g. SymMatrix (company Symrise, INCI: Maltodextrin, *Rubus Fruticosus* (Blackberry) Leaf Extract). Preferred actives of are selected from the group consisting of retinyl palmitate, ursolic acid, extracts from the leaves of the Rosaceae family, sub-family Rosoideae, genistein and daidzein.

(iii) Skin-moisturizing agents. Preferred skin moisturizing agents are selected from the group consisting of alkane diols or alkane triols comprising 3 to 12 carbon atoms, preferably $C_3$-$C_{10}$-alkane diols and $C_3$-$C_{10}$-alkane triols. More preferably the skin moisturizing agents are selected from the group consisting of: glycerol, 1,2-propylene glycol, 1,2-butylene glycol, 1,3-butylene glycol, 1,2-pentanediol, 1,2-hexanediol, 1,2-octanediol and 1,2-decanediol.

(iv) Glycosaminoglycan stimulators. Preferred compositions comprise substances stimulating the synthesis of glycosaminoglycans selected from the group consisting of hyaluronic acid and derivatives or salts, Subliskin (Sederma, INCI: Sinorhizobiunn Meliloti Ferment Filtrate, Cetyl Hydroxyethylcellulose, Lecithin), Hyalufix (BASF, INCI: Water, Butylene Glycol, *Alpinia galanga* leaf extract, Xanthan Gum, Caprylic/Capric Triglyceride), Stimulhyal (Soliance, INCI: Calcium ketogluconate), Syn-Glycan (DSM, INCI: Tetradecyl Aminobutyroylvalylaminobutyric Urea Trifluoroacetate, Glycerin, Magnesium chloride), Kalpariane (Biotech Marine), DC Upregulex (Distinctive Cosmetic Ingredients, INCI: Water, Butylene Glycol, Phospholipids, Hydrolyzed Sericin), glucosamine, N-acetyl glucosamine, retinoids, preferably retinol and vitamin A, *Arctium lappa* fruit extract, *Eriobotrya japonica* extract, Genkwanin, N-Methyl-L-serine, (−)-alpha-bisabolol or synthetic alpha-bisabolol such as e.g. Dragosantol and Dragosantol 100 from Sym rise, oat glucan, *Echinacea purpurea* extract and soy protein hydrolysate. Preferred actives are selected from the group consisting of hyaluronic acid and derivatives or salts, retinol and derivatives, (−)-alpha-bisabolol or synthetic alpha-bisabolol such as e.g. Dragosantol and Dragosantol 100 from Symrise, oat glucan, *Echinacea purpurea* extract, Sinorhizobiunn Meliloti Ferment Filtrate, Calcium ketogluconate, *Alpinia galanga* leaf extract and tetradecyl aminobutyroylvalylaminobutyric urea trifluoroacetate.

(v) Anti-inflammatory agents. The compositions may also contain anti-inflammatory and/or redness and/or itch ameliorating ingredients, in particular steroidal substances of the corticosteroid type selected from the group consisting of hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Non-steroidal anti-inflammatories can also be used. Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid derivatives, in particular avenanthramides described in WO 2004 047833 A1, are preferred anti-itch ingredients in a composition according to the present invention. Also useful are natural or naturally occurring anti-inflammatory mixtures of substances or mixtures of substances that alleviate reddening and/or itching, in particular extracts or fractions from *camomile, Aloe vera, Commiphora* species, *Rubia* species, willow, willowherb, oats, *calendula, arnica*, St John's wort, honeysuckle, rosemary, *Passiflora incarnata*, witch hazel, ginger or *Echinacea*; preferably selected from the group consisting of extracts or fractions from *camomile, Aloe vera*, oats, *calendula, arnica*, honeysuckle, rosemary, witch hazel, ginger or *Echinacea*, and/or pure substances, preferably alpha-bisabolol, apigenin, apigenin-7-glucoside, gingerols, shogaols, gingerdiols, dehydrogingerdiones, paradols, natural or naturally occurring avenanthramides, preferably tranilast, avenanthramide A, avenanthramide B, avenanthramide C, non-natural or non-naturally occurring avenanthramides, preferably dihydroavenanthramide D, dihydroavenanthramide E, avenanthramide D, avenanthramide E, avenanthramide F, boswellic acid, phytosterols, glycyrrhizin, glabridin and licochalcone A; preferably selected from the group consisting of alpha-bisabolol, natural avenanthramides, non-natural avenanthramides, preferably dihydroavenanthramide D (as described in WO 2004 047833 A1), boswellic acid, phytosterols, glycyrrhizin, and licochalcone A, and/or allantoin, panthenol, lanolin, (pseudo-)ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, phytosterols, chitosan, mannose, lactose and (β-glucans, in particular 1,3-1,4-β-glucan from oats.

When bisabolol is used in the context of the present invention it can be of natural or synthetic origin, and is preferably "alpha-bisabolol". Preferably, the bisabolol used is synthetically prepared or natural (−)-alpha-bisabolol and/or synthetic mixed-isomer alpha-bisabolol. If natural (−)-alpha-bisabolol is used, this can also be employed as a constituent of an essential oil or of a plant extract or of a fraction thereof, for example as a constituent of (fractions of) oil or extracts of camomile or of *Vanillosmopsis* (in particular *Vanillosmopsis erythropappa* or *Vanillosmopsis arborea*). Synthetic alpha-bisabolol is obtainable, for example, under the name "Dragosantol" from Symrise.

In case ginger extract is used in the context of the present invention, preferably extracts of the fresh or dried ginger root are used which are prepared by extraction with methanol, ethanol, iso-propanol, acetone, ethyl acetate, carbon dioxide (CO2), hexane, methylene chloride, chloroform or other solvents or solvent mixtures of comparable polarity. The extracts are characterized by the presence of active skin irritation-reducing amounts of constituents such as e.g. gingerols, shogaols, gingerdiols, dehydrogingerdiones and/or paradols.

(vi) TRPV1 antagonists. Suitable compounds which reduce the hypersensitivity of skin nerves based on their action as TRPV1 antagonists, encompass e.g. trans-4-tert-butyl cyclohexanol as described in WO 2009 087242 A1, or indirect modulators of TRPV1 by an activation of the μ-receptor, e.g. acetyl tetrapeptide-15, are preferred.

(vii) Desquamating agents. The compositions may also contain desquamating agents (component b5) in amounts of about 0.1 to about 30% b.w. preferably about 0.5 to about 15% b.w., particularly preferably about 1 to about 10% b.w. based on the total weight of the preparation. The expression "desquamating agent" is understood to mean any compound capable of acting:

either directly on desquamation by promoting exfoliation, such as (3-hydroxy acids, in particular salicylic acid and its derivatives (including 5-n-octanoylsalicylic acid); α-hydroxy acids, such as glycolic, citric, lactic, tartaric, malic or mandelic acids; urea; gentisic acid; oligofucoses; cinnamic acid; extract of *Sophora japonica*; resveratrol and some derivatives of jasnnonic acid;

or on the enzymes involved in the desquamation or the degradation of the corneodesmosomes, glycosidases, stratum corneum chymotryptic enzyme (SCCE) or other proteases (trypsin, chymotrypsin-like). There may be mentioned agents chelating inorganic salts: EDTA; N-acyl-N,N',N'-ethylenediaminetriacetic acid; aminosulphonic compounds and in particular (N-2-hydroxyethylpiperazine-N-2-ethane)sulphonic acid (HEPES); derivatives of 2-oxothiazolidine-4-carboxylic acid (procysteine); derivatives of alpha-amino acids of the glycine type (as described in EP-0 852 949, and sodium methylglycine diacetate marketed by BASF under the trade name TRILON M); honey; sugar derivatives such as O-octanoyl-6-D-maltose and N-acetylglucosamine; chestnut extracts such as those marketed by the company SILAB under the name Recoverine®, prickly pear extracts such as those marketed under the name Exfolactive® by the company SILAB, or Phytosphingosine SLC® (phytosphingosine grafted with a salicylic acid) marketed by the company Degussa.

Desquamating agents suitable for the invention may be chosen in particular from the group comprising sulphonic acids, calcium chelators, α-hydroxy acids such as glycolic, citric, lactic, tartaric, malic or mandelic acids; ascorbic acid and its derivatives such as ascorbyl glucoside and magnesium ascorbyl phosphate; nicotinamide; urea; (N-2-hydroxyethylpiperazine-N-2-ethane)sulphonic acid (HEPES), β-hydroxy acids such as salicylic acid and its derivatives, retinoids such as retinol and its esters, retinal, retinoic acid and its derivatives, those described in the documents FR 2570377 A1, EP 0199636 A1, EP 0325540 A1, EP 0402072 A1, chestnut or prickly pear extracts, in particular marketed by SILAB; reducing compounds such as cysteine or cysteine precursors.

Desquamating agents which can be used are also nicotinic acid and its esters and nicotinamide, also called vitamin B3 or vitamin PP, and ascorbic acid and its precursors, as described in particular in application EP 1529522 A1.

(viii) Anti-cellulite agents. Anti-cellulite agents and lipolytic agents are preferably selected from the group consisting of those described in WO 2007/077541, and beta-adrenergic receptor agonists such as synephrine and its derivatives, and cyclohexyl carbamates described in WO 2010/097479. Agents enhancing or boosting the activity of anti-cellulite agents, in particular agents which stimulate and/or depolarise C nerve fibres, are preferably selected from the group consisting of capsaicin and derivatives thereof, vanillyl-nonylamid and derivatives thereof, L-carnitine, coenzym A, isoflavonoides, soy extracts, *ananas* extract and conjugated linoleic acid.

(ix) Fat enhancing agents. Formulations and products according to the present invention may also comprise one or more fat enhancing and/or adipogenic agents as well as agents enhancing or boosting the activity of fat enhancing agents. A fat enhancing agent is for example hydroxymethoxyphenyl propylmethylmethoxybenzofuran (trade name: Sym3D®).

A.14 Hair Growth Activators or Inhibitors

Formulations and products according to the present invention may also comprise one or more hair growth activators, i.e. agents to stimulate hair growth. Hair growth activators are preferably selected from the group consisting of pyrimidine derivatives such as 2,4-diaminopyrimidine-3-oxide (Aminexil), 2,4-diamino-6-piperidinopyrimidine-3-oxide (Minoxidil) and derivatives thereof, 6-amino-1,2-dihydro-1-hydroxy-2-imino-4-piperidinopyrimidine and its derivatives, xanthine alkaloids such as caffeine, theobromine and theophylline and derivatives thereof, quercetin and derivatives, dihydroquercetin (taxifolin) and derivatives, potassium channel openers, antiandrogenic agents, synthetic or natural 5-reductase inhibitors, nicotinic acid esters such as tocopheryl nicotinate, benzyl nicotinate and C1-C6 alkyl nicotinate, proteins such as for example the tripeptide Lys-Pro-Val, diphencypren, hormons, finasteride, dutasteride, flutamide, bicalutamide, pregnane derivatives, progesterone and its derivatives, cyproterone acetate, spironolactone and other diuretics, calcineurin inhibitors such as FK506 (Tacrolimus, Fujimycin) and its derivatives, Cyclosporin A and derivatives thereof, zinc and zinc salts, polyphenols, procyanidins, proanthocyanidins, phytosterols such as for example beta-sitosterol, biotin, eugenol, (±)-beta-citronellol, panthenol, glycogen for example from mussels, extracts from microorganisms, algae, plants and plant parts of for example the genera dandelion (Leontodon or Taraxacum), Orthosiphon, Vitex, *Coffea, Paullinia, Theobroma, Asiasarum, Cucurbita* or *Styphnolobium, Serenoa repens* (saw palmetto), *Sophora flavescens, Pygeum africanum, Panicum miliaceum, Cimicifuga racemosa, Glycine max, Eugenia caryophyllata, Cotinus coggygria, Hibiscus rosa-sinensis, Camellia sinensis, Ilex paraguariensis, Isochrysis galbana*, licorice, grape, apple, barley or hops or/nd hydrolysates from rice or wheat.

Alternatively, formulations and products according to the present invention may comprise one or more hair growth inhibitors (as described above), i.e. agents to reduce or prevent hair growth. Hair growth inhibitors are preferably selected from the group consisting of activin, activin derivatives or activin agonists, ornithine decarboxylase inhibitors such as alpha-difluoromethylornithine or pentacyclic triterpenes like for example ursolic acid, betulin, betulinic acid, oleanolic acid and derivatives thereof, 5alpha-reductase inhibitors, androgen receptor antagonists, S-adenosylmethionine decarboxylase inhibitors, gamma-glutamyl transpeptidase inhibitors, transglutaminase inhibitors, soybean-derived serine protease inhibitors, extracts from microorganisms, algae, different microalgae or plants and plant parts of for example the families Leguminosae, Solanaceae, Graminae, Asclepiadaceae or Cucurbitaceae, the genera *Chondrus, Gloiopeltis, Ceramium, Durvillea, Glycine max, Sanguisorba officinalis, Calendula officinalis, Hamamelis virginiana, Arnica montana, Salix alba, Hypericum perforatum* or *Gymmenna sylvestre*.

A.15 Cooling Agents

The compositions may also contain one or more substances with a physiological cooling effect (cooling agents), which are preferably selected here from the following list: menthol and menthol derivatives (for example L-menthol, D-menthol, racemic menthol, isomenthol, neoisomenthol, neomenthol) menthylethers (for example (1-menthoxy)-1,2-propandiol, (l-menthoxy)-2-methyl-1,2-propandiol, 1-menthyl-methylether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxy)acetate, menthylpyroglutamate), menthylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example monomenthylsuccinate, mono-menthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or $N^\alpha$-(menthanecarbonyl)glycmethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005 049553 A1, methanecarboxylic acid-N(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (I-(–)-isopulegol, I-(–) isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl)ethyl)-3-p-menthanecarboxamide or related compounds), (1R,2S,5R)—N-(4-Methoxyphenyl)-5-methyl-2-(1-isopropyl)cyclohexane-carboxamide [WS12], oxamates (preferably those described in EP 2033688 A2).

A.16 Anti-Microbial Agents

Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chloro-phenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

A.17 Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

A.18 Odour Absorbers and Antiperspirant Active Agents

Suitable odour absorbers are substances which are able to absorb and largely retain odour-forming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of *labdanum* or *styrax* or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniperberry oil, vetiver oil, olibanum oil, galbanum oil, *labdanum* oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine.

A.19 Film Formers and Anti-Dandruff Agents

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

A.20 Carriers and Hydrotropes

Preferred cosmetics carrier materialsare solid or liquid at 25° C. and 1013 mbar (including highly viscous substances) as for example glycerol, 1,2-propylene glycol, 1,2-butylene glycol, 1,3-propylene glycol, 1,3-butylene glycol, ethanol, water and mixtures of two or more of said liquid carrier materials with water. Optionally, these preparations according to the invention may be produced using preservatives or solubilizers. Other preferred liquid carrier substances, which may be a component of a preparation according to the invention are selected from the group consisting of oils such as vegetable oil, neutral oil and mineral oil.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

In addition, hydrotropes, for example ethanol, isopropyl alcohol or polyols, may be used to improve flow behaviour. Suitable polyols preferably contain 2 to 15 carbon atoms and at least two hydroxyl groups. The polyols may contain other functional groups, more especially amino groups, or may be modified with nitrogen. Typical examples are
glycerol;
alkylene glycols such as, for example, ethylene glycol, diethylene glycol, propylene glycol, butylene glycol, hexylene glycol and polyethylene glycols with an average molecular weight of 100 to 1000 Dalton;
technical oligoglycerol mixtures with a degree of self-condensation of 1.5 to 10, such as for example technical diglycerol mixtures with a diglycerol content of 40 to 50% by weight;
methylol compounds such as, in particular, trimethylol ethane, trimethylol propane, trimethylol butane, pentaerythritol and dipentaerythritol;
lower alkyl glucosides, particularly those containing 1 to 8 carbon atoms in the alkyl group, for example methyl and butyl glucoside;
sugar alcohols containing 5 to 12 carbon atoms, for example sorbitol or mannitol,
sugars containing 5 to 12 carbon atoms, for example glucose or sucrose;
amino sugars, for example glucamine;
dialcoholamines, such as diethanolamine or 2-aminopropane-1,3-diol.

A.21 Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

A.22 Perfume Oils and Fragrances

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, *costus*, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

A.23 Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. Advantageous coloured pigments are for example titanium dioxide, mica, iron oxides (e.g. $Fe_2O_3$ $Fe_3O_4$, FeO(OH)) and/or tin oxide. Advantageous dyes are for example carmine, Berlin blue, chromium oxide green, ultramarine blue and/or manganese violet.

A.24 Preparations

Preferred compositions according to the present inventions are selected from the group of products for treatment, protecting, care and cleansing of the skin and/or hair or as a make-up product, preferably as a leave-on product (meaning that the one or more compounds of formula (I) stay on the skin and/or hair for a longer period of time, compared to rinse-off products, so that the moisturizing and/or anti-ageing and/or wound healing promoting action thereof is more pronounced).

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or postfoaming), a deodorant and/or antiperspirant, mouthwash and mouth rinse, a foot care product (including keratolytic, deodorant), an insect repellent, a sunscreen, aftersun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a solution e.g. in oil (fatty oils or fatty acid esters, in particular $C_6$-$C_{32}$ fatty acid $C_2$-$C_{30}$ esters)) or silicone oil, or a spray (e.g. pump spray or spray with propellant).

Auxiliary substances and additives can be included in quantities of 5 to 99% b.w., preferably 10 to 80% b.w., based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99% b.w., preferably 5 to 80% b.w., based on the total weight of the preparation.

INDUSTRIAL APPLICATION

Another object of the present invention refers to a non-therapeutic method for whitening human skin or hair by topical administration of a working amount of either the mixture comprising said components (a), (b) and optionally (c) or the composition comprising said mixture. Preferably human skin or hair is treated with an amount of from about 0.1 to about 10% b.w. and preferably about 0.05 to about 5% b.w. of the mixture of components (a), (b) and optionally (c).

Finally, the invention relates to the use of a mixture comprising (a) resorcinol derivatives of formula (I)

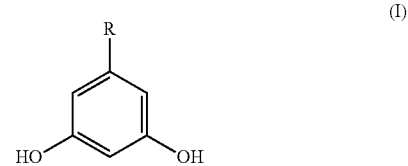

(I)

in which R stands for an alkyl radical having 3 to 10 carbon atoms or an optionally substituted alkylphenyl radical having 8 to 16 carbon atoms, and (b) bisabolol, and optionally (c) alkandiols having 3 to 10 carbon atoms.

as a skin or hair whitening agent. Preferably the mixture is applied to human skin or hair in an amount of from about 0.1 to about 10% b.w. and preferably from about 0.05 to about 5% b.w.

EXAMPLES

Examples 1 to 4, Comparative Examples C1 to C4

To evaluate the lightening efficacy of the test products an ex-vivo study using human full-thickness skin explants was performed. In two different phenotypes (pigmentation scale:

very light<light<intermediate<tanned<brown<dark), light and dark, the products applied in emulsion showed a significant reduction of melanin content after 6 days. Phenylethyl Resorcinol and Bisabolol were tested in the ex-vivo human skin explant model using a "tanned" phototype. 1,2-Pentandiol was added to some of the blends to improve the penetration of the active ingredients into the skin layers.

Table 1 shows how the melanin decrease into the skin explants was improved despite the absence of efficacy of Bisabolol alone. Bisabolol has been reported in the literature to have whitening activity in vivo. In our ex vivo model 0.08% Bisabolol did not have any efficacy. 0.4% of Phenelethyl Resorcinol exhibited a melanin decrease of 21% whereas the mixture of 0.2% and 0.4% Phenylethyl Resorcinol, respectively and 0.04% Bisabolol showed a melanin decrease of 15% and 25% respectively. The combination of Phenylethyl Resorcinol and Bisabolol in 1,2 Pentandiol resulted in an even stronger melanin decrease of 28% and 33% respectively, demonstrating that the synergism between the ingredients allows an enhanced efficacy with a reduced dosage of the active principles. Examples 1 to 4 are according to the invention, Examples C1 to C4 serve for comparison.

TABLE 1

Melanin semi-quantitative evaluation: comparison of treatments versus placebo at day 6 (phototype: tanned)

| | Compound | | | | | | | |
|---|---|---|---|---|---|---|---|---|
| | C1 | C2 | C3 | 1 | 2 | 3 | 4 | C4 |
| Placebo (Standard) | 0.4 | — | — | — | — | — | — | — |
| Phenylethyl Resorcinol | — | 0.2 | 0.4 | 0.2 | 0.4 | 0.2 | 0.4 | — |
| Bisabolol | — | — | — | 0.04 | 0.04 | 0.04 | 0.04 | 0.08 |
| 1,2-Pentandiol | — | — | — | — | — | 40.0 | 40.0 | — |
| | Melanin reduction | | | | | | | |
| Amount (g) | 36 | | | | | | | 36 |
| Reduction vs. Standard (%) | 0 | −13 | −21 | −15 | −25 | −28 | −33 | 0 |

Examples 5 to 8

To confirm the multiple benefits of the combination a clinical test was performed in wintertime in Shanghai with 21 female Chinese subjects with at least one dark spot on the face larger than 5 mm. The evaluation of the depigmenting effect based on triplicate colorimetric measurements was carried out on a selected dark spot and adjacent site on face using Chromameter®, Mexameter® and Photographies under standardized conditions.

Subjects applied the placebo formulation twice daily from day 1 to day 28 on the whole face (spot+adjacent zone). After a wash out period of 21 days, they applied twice daily 4% SymWhite PLUS, a blend containing 10% Phenylethyl Resorcinol, 2% Bisabolol and 40% Pentylene glycol, from day 50 to day 78 on the whole face (same spot and adjacent zone than placebo). With this protocol placebo and tested formulation were applied on the same spot and face area. After 28 days of treatment the tested product had a statistically significant depigmenting effect on dark spots comparatively to placebo. 86% of the subjects assessed their dark spots and imperfections as reduced. Moreover, 90% reported that their complexion would be less dull, brighter, more uniform and luminous.

Formulation Examples

In the following several examples are presented how to incorporate the mixtures according to the invention into cosmetic compositions. If not indicated otherwise, the different phases are prepared separately and then blended one after another.

Formulation 1

APD Aerosol (amounts in % b.w.)

| Phase | Product | INCI | Amount |
|---|---|---|---|
| A | Myglyol ® 840 Gel B | Propylene Glycol Dicaprylate, Dicaprate Steralkonium Hectorite, Propylene Carbonate | 1.50 |
| | Xiameter ® PMX 0245 Cycloxiloxane | Cyclopentansiloxane | 8.00 |
| | Dow Corning 1401 Fluid | Cyclomethicone Dimethiconol | 4.50 |
| | Symwhite ® 377 | Phenylethyl Resorcinol | 0.50 |
| | Dragosantol ® 100 | Bisabolol | 0.05 |
| | Hydrolite ® 5 | Pentylene Glycol | 1.00 |
| | Neo Heliopan ® BB | Benzophenone-3 | 0.50 |
| | Locron ® P | Aluminium Chlorohydrate | 10.00 |
| B | Propellant 2.7 bar | | Ad 100 |

Formulation 2

Aerosol Deo Spray (amounts in % b.w.)

| Phase | Product | INCI | Amount |
|---|---|---|---|
| A | Water | Aqua | Ad 100 |
| | EDTA | Disodium EDTA | 0.10 |
| B | Symwhite ® 377 | Phenylethyl Resorcinol | 0.50 |
| | Dragosantol ® 100 | Bisabolol | 0.05 |
| | Hydrolite ® 5 | Pentylene Glycol | 0.100 |
| | Sym Deo 125 | 2-Methyl-5-Cyclohexylpentanol | 0.50 |
| | Solubilizer | PEG-40 Hydrogenated Castor Oil, Trideceth-9, Propylene Glycol, Water | 2.00 |
| | Cibafest H liquid | Sodium Benzotriazolyl Butylphenol Sulfonate, Buteth-3, Tributyl Citrate, Butoxytriglycol | 0.50 |
| C | Ethanol | Alcoohol denat. | 40.00 |
| D | Citric acid | | 0.45 |

Formulation 3

Deo roll on (amounts in % b.w.)

| Phase | Product | INCI | Amount |
|---|---|---|---|
| A | Symwhite ® 377 | Phenylethyl Resorcinol | 0.30 |
| | Dragosantol ® 100 | Bisabolol | 0.03 |
| | Hydrolite ® 5 | Pentylene Glycol | 0.80 |

| Phase | Product | INCI | Amount |
|---|---|---|---|
| | Symsitive ® | Pentylene glycol, 4-t-butylcyclohexanol | 1.20 |
| | Neo Heliopan ® BB | Benzophenone-3 | 0.50 |
| | Copherol ® 1250 | Tocopheryl Acetate | 0.50 |
| | Arlacel ® 165 | PEG-100 Stearate, Glyceryl Stearate | 3.00 |
| | Brij ® 721 | Steareth-21 | 2.50 |
| | Arlamol ® PS 15 | PEG 15 Stearyl ether | 2.00 |
| | Lanette ® O | Cetearyl alcohol | 1.00 |
| | Brij ® 72 | Steareth-2 | 0.3 |
| B | Water | Aqua | Ad 100 |
| | Veegum ® HV | Magnesium Aluminium Silicate | 1.00 |
| | Glycerine 99.5 | Glycerin | 2.00 |
| | SymTriol ® | Caprylyl Glycol, 1,2-Hexanediol, Methylbenzyl Alcohol | 0.60 |
| | EDTA | Disodium EDTA | 0.10 |
| C | Covastyle ® MBS | | 0.15 |
| | Water | Aqua | 3.00 |
| D | Oxynex ® ST liquid | Diethylhexyl Springylidenemalonate, Caprylic Capric Triglyceride | 0.10 |
| | Sym Deo 125 | 2-Methyl-5-Cyclohexylpentanol | 0.5 |

Formulation 4
Deo roll on (amounts in % b.w.)

| Phase | Product | INCI | Amount |
|---|---|---|---|
| A | Symwhite ® Plus | Phenylethyl Resorcinol, Bisabolol, Pentylene, Glycol, Capric Caprylic Triglyceride | 1.00 |
| | Neo Heliopan ® BB | Benzophenone-3 | 0.50 |
| | Copherol ® 1250 | Tocopheryl Acetate | 0.50 |
| | Arlacel ® 165 | PEG-100 Stearate, Glyceryl Stearate | 3.00 |
| | Brij ® 721 | Steareth-21 | 2.50 |
| | Arlamol ® PS 15 | PPG 15 Stearyl Ether | 2.00 |
| | Lanette ® O | Cetearyl Alcohol | 1.00 |
| | Brij ® 72 | Steareth-2 | 0.30 |
| | Water | Aqua | Ad 100 |
| B | Veegum ® HV | Magnesium Aluminium Silicate | 1.00 |
| | Glycerin 99.5 | | 2.00 |
| | Sym Triol ® | Caprylyl Glycol, 1,2-Hexandiol, Methylbenzyl Alcohol | 0.6 |
| | EDTA | Disodium EDTA | 0.1 |
| C | Covastyle ® MBS | Sodium Metabisulfite | 0.15 |
| | Waster | Aqua | 3.00 |
| D | Oxynex ® ST liquid | Diethylhexyl Springylidenemalonate, Caprylic Capric Triglyceride | 0.10 |
| | Sym Deo MPP | | 0.3 |

Formulation 5
Moisturizing balm (amounts in % b.w.)

| Phase | Product | INCI | Amount |
|---|---|---|---|
| A | Symwhite ® Plus | Phenylethyl Resorcinol, Bisabolol, Pentylene Glycol, Capric Caprylic Triglyceride | 5.00 |
| | Neo Heliopan ® BB | Benzophenone-3 | 0.25 |
| | SymMollient ® S | Cetearyl Nonanoate | 1.50 |
| | Dragoxat ® 89 | Ethylhexyl Isononanoate | 3.00 |
| | PCL Liquid | Cetearyl Ethylhexanoate, Isopropyl Myriistate | 5.00 |
| | Copherol ® 1250 | Tocopheryl Acetate | 0.50 |
| | Aristoflex ® AVC | Ammonium Acryloldimethyltaurate/VP Copolymer | 1.50 |
| | Fragrance | Parfum | 0.50 |
| B | Water | Aqua | Ad 100 |
| | Hydrolite ® 5 | Pentylene Glycol | 5.00 |
| C | Water | Aqua | 3.00 |
| | Covastyle ® MBS | Sodium Metabisulfite | 0.150 |
| D | Oxynex ® ST liquid | Diethylhexyl Springylidenemalonate, Caprylic Capric Triglyceride | 0.10 |

Formulation 6
Hand repair cream (amounts in % b.w.)

| Phase | Product | INCI | Amount |
|---|---|---|---|
| A | Symwhite ® Plus | Phenylethyl Resorcinol, Bisabolol, Pentylene Glycol, Capric Caprylic Triglyceride | 5.00 |
| | Dracorine ® CE | Glyceryl Stearate Citrate | 2.00 |
| | Cutina ® GMS-V | Glyceryl Stearate | 2.00 |
| | Lanette ® O OR | Cetearyl Alcohol | 2.70 |
| | Light Mineral Oil | Mineral Oil | 3.00 |
| | Neo Heliopan ® BB | Benzophenone-3 | 0.30 |
| | Neutral Oil | Caprylic/Capric Triglyceride | 4.00 |
| | Dragoxat ® 89 | Ethylhexyl Nonanoate | 1.00 |
| | SymRepair ® 100 | Hexyldecanol, Bisabolol, Cetylhydroxyproline Palmitamide, Stearic Acid, *Brassica Campestris* (Rapeseed) Sterols | 0.20 |
| | Copherol ® 1250 | Tocopheryl Acetate | 0.50 |
| | Xiameter ® PMX-200 Silicone Fluid 350CS | Dimethicone | 1.50 |
| B | Water | Aqua | Ad 100 |
| | Glycerin 99.5 P | | 6.00 |
| | SymDiol ® 68 | 1,2-Hexanediol, Caprylyl Glycol | 0.80 |
| | Edeta ® BD | Disodium EDTA | 0.10 |
| C | Simulgel ® NS | Hydroxyethyl Acrylate/Sodium Acryloyldimethyl Taurate Copolymer, Squalane, Polysorbate-60 | 2.00 |
| D | Water | Aqua | 3.00 |
| | Covastyle ® MBS | Sodium Metabisulfite | 0.15 |
| E | Oxynex ® ST liquid | Diethylhexyl Syringylidenemalonate, Caprylic/Capric Triglycerides | 0.30 |
| F | Fragrance | Parfum | 0.5 |

Formulation 7
Hydrogel (amounts in % b.w.)

| Phase | Product | INCI | Amount |
|---|---|---|---|
| A | Water | Aqua | Ad 100 |
| B | PCL Liquid 100 | Cetearyl Ethylhexanoate | 3.00 |
|   | Lanette ® O | Cetearyl Alcohol | 4.00 |
|   | Paraffin Oil White | Paraffinum Liquidum | 3.00 |
|   | Eutanol ® G | Octyldodecanol | 4.00 |
|   | Xiameter ® PMX-200 Silicone Fluid | Dimethicone | 0.50 |
|   | Symwhite ® Plus | Phenylethyl Resorcinol, Bisabolol, Pentylene Glycol, Capric Caprylic Triglyceride | 4.00 |
|   | Neo Heliopan ® BB | Benzophenone-3 | 0.25 |
| C | Pemulen ® TR-1 | Acrylates/C10-30 Alkyl Acrylate Cross-polymer | 0.25 |
|   | Carbopol ® Ultrez 21 | Acrylates/C10-30 Alkyl Acrylate Cross-polymer | 0.30 |
| D | Sodium Hydroxide 10% solution | Sodium Hydroxide | 0.68 |
| E | Water | Aqua | 2.00 |
|   | Covastyle ® MBS | Sodium Metabisulfite | 0.08 |
|   | Oxynex ® ST liquid | Diethylhexyl Syringylidenemalonate, Caprylic/Capric Triglycerides | 0.30 |

Formulation 8
BB Cream (amounts in % b.w.)

| Phase | Product | INCI | Amount |
|---|---|---|---|
| A | Emulsiphos ® | Potassium Cetyl Phosphate, Hydrogenated Palm Gl<ycosides | 2.00 |
|   | Isodragol ® | Triisononanoin | 2.50 |
|   | Dragoxat 89 | Ethylhexyl Isononanoate | 1.00 |
|   | Lanette ® O | Cetearyl Alcohol | 2.00 |
|   | Xiameter ® PMX-200 Silicone Fluid | Dimethicone | 1.00 |
|   | SymMollient ® S | Cetearyl Nonanoate | 1.00 |
|   | SymHelios ® 1031 | Benzylidene Dimethoxydimethylin danone | 0.20 |
|   | Neo Heliopan ® OS | Ethylhexyl Salicylate | 2.00 |
|   | Neo Heliopan ® HMS | Homosalate | 1.00 |
|   | Neo Heliopan ® 357 | Butyl Methoxydibenzoylmethane | 1.00 |
|   | Symwhite ® Plus | Phenylethyl Resorcinol, Bisabolol, Pentylene Glycol, Capric Caprylic Triglyceride | 3.00 |
|   | Eumulgin ® SG | Sodium Stearoyl Glutamate | 0.20 |
|   | Copherol ® 1250 | Tocopheryl Acetate | 0.10 |
|   | EDTA NA2 | Disodium EDTA | 0.10 |
| B | Keltrol ® CG-T | Xanthan Gum | 0.30 |
|   | Carbopol ® Ultrez 21 | Acrylates/C10-30 Alkyl Acrylate Cross-polymer | 0.15 |
|   | Micropoly 250S | Polyethylene | 0.70 |
| C | Water | Aqua | Ad 100 |
|   | Glycerin | Glycerin | 3.00 |
|   | SymOcide ® PS | Phenoxyethanol, Decylene Glycol, 1,2-Hexandiol | 0.80 |
| D | Cosmetic Color Brown Powder | Titanium Dioxide (and) Iron Oxides | 1.00 |
|   | Food Color Iron Oxide Yellow | Iron Oxides | 0.05 |
|   | Food Color Titanium Dioxide | Titanium Dioxide | 0.15 |
| E | Dragosine ® | Carnosin | 0.10 |
|   | Hydroviton ® plus 2290 | Water, Pentylene Glycol, Glycerin, Fructose, Urea, Citric Acid, Sodium Hydroxide, Maltose, Sodium PCA, Sodium Chloride, Sodium Lactate, Trehalose, Allantoin, Sodium Hyaluronate, Glucose | |
|   | Oxynex ® ST liquid | Diethylhexyl Syringylidenemalonate, Caprylic/Capric Triglycerides | 0.10 |
|   | Actipone ® Sweet Cherry Tree Wood | Propylene Glycol, water, *Prunus Avium* Wood Extract | 0.2 |

Formulations 9 to 19
Skin Whitening Compositions

| Ingredients | INCI-Name | 9 | 10 | 11 | 12 | 13 | 14 | 15 | 16 | 17 | 18 | 19 |
|---|---|---|---|---|---|---|---|---|---|---|---|---|
| | | Skin whitening ingredients | | | | | | | | | | |
| Sclareolide | Sclareolide | 0.1 | 1 | 0.05 | 0.2 | 1 | 0.5 | 0.02 | 0.5 | 0.2 | 1 | 0.5 |
| SymWhite 377 (Symrise) | Phenylethyl resorcinol | 0.5 | 0.5 | 0.5 | 0.5 | 0.1 | 0.2 | 0.1 | 0.1 | 0.2 | 0.2 | 0.5 |
| beta-Arbutin | Arbutin | | | | | 0.5 | | | | | | |
| Nicotinamide | Niacinamide | | | | 0.5 | | | | | | 1 | |
| Kojic acid | Kojic acid | | | 0.5 | | | | | | | | 1 |
| Mg ascorbyl phosphate | Magnesium ascorbyl phosphate | | | 5 | | | | | | | 3 | |

| Ingredients | INCI-Name | 9 | 10 | 11 | 12 | 13 | 14 | 15 | 16 | 17 | 18 | 19 |
|---|---|---|---|---|---|---|---|---|---|---|---|---|
| Actipone ® Mulberry GW (Symrise) | Aqua, Glycerin, *Morus Alba* Root Extract | 2 | | | | | | | | | | |
| (3-Methoxy-propyl)-carbamic acid (1R,2S,5R)-2-isopropyl-5-methyl-cyclohexylester | | | | | | | | | | | 0.5 | |
| p-Tolyl-carbamic acid 3,5-dimethyl-cyclohexyl ester | | 1 | | | | | | | | | | |
| (2-Methoxy-phenyl)-carbamic acid 3,3,5-trimethyl-cyclohexyl ester | | | | | | | | | | 0.5 | | |

| Ingredients | INCI-Name | 9 | 10 | 11 | 12 | 13 | 14 | 15 | 16 | 17 | 18 | 19 |
|---|---|---|---|---|---|---|---|---|---|---|---|---|
| *Other Ingredients* | | | | | | | | | | | | |
| (—) alpha Bisabolol nat. | Bisabolol | | | 0.1 | | 0.2 | | | | | 0.1 | |
| Abil 350 | Dimethicone | | | | 2 | | | | | | | |
| Actipone ® Laminaria SaccharinaGW | Glycerin, Water (Aqua), *Laminaria Saccharina* Extract | | | | | | 1 | | | | | |
| *Aloe Vera* Gel Conc.10:1 | *Aloe Barbadensis* Leaf Juice | | | 1 | | | | | | | | |
| Aluminium Stearate | Aluminium Stearate | | | | | | | | 1.2 | | | |
| Amaze XT | Dehydroxanthan Gum | 1.4 | | | | | | | | | | |
| Betulin 90% (1079) | Betulin | | | | | 0.15 | | | | | | |
| Biotive ® L-Arginine | Arginine | 3.2 | 0.5 | 0.6 | 0.9 | | | | | | | |
| Biotive ® Troxerutin | Troxerutin | | 0.5 | 0.5 | | | | | | | | |
| Carbopol ETD 2020 | Acrylates/C10-30 Alkyl Acrylate Crosspolymer | 0.2 | | | | | | | | | | |
| Carbopol ETD 2050 | Carbomer | | | | 0.2 | | 0.2 | | | | | |
| Carbopol Ultrez-21 | Acrylates/C10-30 Alkyl Acrylate Crosspolymer | | | | | 0.5 | | | | | | |
| Citric Acid 10% sol. in water | Citric Acid | | | | | | | | | 3.1 | | |
| Comperlan 100 | Cocamide MEA | | | | | | | | | 1 | | |
| Corapan TQ | Diethylhexyl 2,6 Naphtalate | | | | | 3 | | | | | | |
| Crinipan ® AD | Climbazole | | | | | | | | | | | 0.1 |
| Cutina GMS V | Glyceryl Stearate | | | | | | 2 | | | | | |
| Cutina PES | Pentaerythrityl Distearate | | | | 2 | | | | | | | |
| Cutina TS | PEG-3 Distearate | | | | | | | | | 2.5 | | |
| DC9701 Cosmetic Powder | Dimethicone/Vinyl Dimethicone Crosspolymer, Silica | | | | | | | | | | 2 | |
| Dermacryl AQF | Acrylates Copolymer | | | | 2 | | | | | | | |
| Dipropylene Glycol | Dipropylene Glycol | | | | | | | | | | | 1 |
| Dow Corning 193 surfactant | PEG-12 Dimethicone | 1 | | | | | | | | | | |
| Dow Corning 246 fluid | Cyclohexa-siloxane | | | | 3 | | 1 | | | | | |
| D-Panthenol 75 L | Panthenol | | | | | | | 1 | | 0.3 | | 0.5 |
| Dracorin ® CE | Glyceryl Stearate/Citrate | | | | | | 3 | | | | | |
| Dracorin ® GOC | Glyceryl Oleate Citrate, Caprylic Capric Triglyceride | | | | | 1.5 | | | | | 0.5 | |
| Drago-Beta-Glucan | Water (Aqua), Butylene Glycol, Glycerin, *Avena Sativa* (Oat) Kernel Extract | | | | | | 1 | | | | | |

| Ingredients | INCI-Name | 9 | 10 | 11 | 12 | 13 | 14 | 15 | 16 | 17 | 18 | 19 |
|---|---|---|---|---|---|---|---|---|---|---|---|---|
| DragoCalm ® | Water, Glycerin, *Avena Sativa* (Oat Kernel Extract) | | | | | | | 1 | | | | |
| Dragocide ® Liquid | Phenoxyethanol, Methylparaben, Ethylparaben, Butylparaben, Propylparaben, Isobutylparaben | | | | | 0.8 | | | | | | |
| Dragoderm ® | Glycerin, *Triticum Vulgare* (Wheat) Gluten, Water (Aqua) | | | | | | 2 | | | | | |
| Dragosan W/O P | Sorbitan Isostearate, Hydrogenated Castor Oil, Ceresin, Beeswax (Cera Alba) | | | | | | | 8 | | | | |
| Dragosantol ® 100 | Bisabolol | | | 0.1 | | | 0.2 | | | | | |
| Dragosine ® | Carnosine | 0.2 | | | | | | 0.2 | | | | |
| Dragoxat ® 89 | Ethylhexyl Isononanoate | | 2 | 5 | | 4 | 7 | | 15 | | 5 | |
| EDTA B | Tetrasodium EDTA | | | | | | | 0.1 | | | | |
| EDTA BD | Disodium EDTA | | 0.1 | 0.1 | 0.1 | | | | | | | 0.1 |
| Emulsiphos ® | Potassium Cetyl Phosphate, Hydrogenated Palm Glycerides | | 2 | 2 | | | | | | | | |
| Ethanol | Ethanol | 10 | | | | | | | | | | |
| Extrapone ® *Ginkgo Biloba* | Propylene Glycol, Water (Aqua), *Ginkgo Biloba* Leaf Extract, Glucose, Lactic Acid | | | | | 1 | | | | | | |
| Food Color Brown E172 + E171 Powder | Color | | | | 2 | | | | | | 3 | |
| Fragrance PFO1 or PFO2 | Parfum | 0.1 | 0.2 | 0.3 | 0.2 | 0.4 | 0.3 | 0.1 | 0.5 | 1 | | 0.1 |
| Frescolat ® MGA | Menthone Glycerin Acetal | | | | | | | 0.1 | | | | |
| Frescolat ® ML | Menthyl Lactate | | | | | | | | | | 0.2 | |
| Fruitapone ® Orange B | Propylene Glycol, Water (Aqua), Citric Acid, *Citrus Aurantium* Dulcis (Orange) Juice, Trideceth-9, Bisabolol | | | | | | | | | | | 0.5 |
| Glycerine 99.5% | Glycerin | 2.5 | 3 | | | 5 | 3 | | | 0.5 | | 10 |
| Hydrolite ®-5 | Pentylene Glycol | 3 | 2 | | 5 | | | | | 1 | | |
| Hydroviton ®-24 | Water, Pentylene Glycol, Glycerin, Lactic Acid, Sodium Lactate, Serine, Urea, Sorbitol, Sodium Chloride, Allantoin | | | | | 1 | 1 | | 10 | | | |
| Iso Adipat | Diisopropyl Adipate | | | | | 1 | | | 5 | | | |
| Isodragol ® | Triisononanoin | | | 2 | | | | | | | | |
| Isopropyl Palmitate | Isopropyl Palmitate | | | | | | | | | | 13 | |
| Jaguar C-162 | Hydroxypropyl Guar, Hydroxypropyltrimonium Chloride | | | | | | | | | 0.1 | | |
| Jojoba Oil | *Simmondsia Chinensis* (Jojoba) Seed Oil | 1 | | | | | 2 | | | | | |
| Keltrol CG RD | Xanthan Gum | | 0.4 | 0.2 | 0.2 | 0.1 | | 0.05 | | | | |
| Lanette 16 | Cetyl Alcohol | | 1 | | | | | | | | | |
| Lanette O | Cetearyl Alcohol | | 0.5 | | | 3 | | | | | 5 | |

| Ingredients | INCI-Name | 9 | 10 | 11 | 12 | 13 | 14 | 15 | 16 | 17 | 18 | 19 |
|---|---|---|---|---|---|---|---|---|---|---|---|---|
| Lara Care A-200 | Galactoarabinan | | 0.3 | | | | | | | | | |
| Luviskol K30 Powder | PVP | | | | | | | | | | | 3 |
| Magnesium Sulfate | Magnesium Sulfate | | | | | | | 0.7 | | | | |
| Mineral Oil | Mineral Oil | | | | | | | 8 | | ad 100 | | |
| Neo Heliopan ® 303 | Octocrylene | | 10 | 4 | | | | | | | 10 | |
| Neo Heliopan ® 357 | Butylmethoxydibenzoylmethane | | 3 | 2 | 3 | | | | | | 5 | |
| Neo Heliopan ® AP | Disodium Phenyl Dibenzimidazole Tetrasulfonate | 3 | | | | | | | | | | |
| Neo Heliopan ® AP, 15% sol., neutralized with Biotive ® L-Arginine | Aqua, Disodium Phenyl Dibenzimidazole Tetrasulfonate, Arginin | | 6.7 | 6.7 | | | | | | | | |
| Neo Heliopan ® E 1000 | Isoamyl p.Methoxycinnamate | | 1 | | | | | | | | | |
| Neo Heliopan ® HMS | Homosalate | | 5 | | 5 | | | | | | | |
| Neo Heliopan ® Hydro, 20% sol., neutralized with Biotive ® L-Arginine | Aqua, Phenylbenzimidazole Sulphonic Acid, Arginin | | 10 | 10 | 10 | | | | | | | |
| Neo Heliopan ® MBC | 4-Methylbenzylidene Camphor | 1 | | | | | | | | | | |
| Neo Heliopan ® OS | Ethylhexyl Salicylate | | | 3 | 5 | | | | | | | |
| Neutral Oil | Caprylic/Capric Triglyceride | | | | | 6 | | | | | 13.7 | |
| Ozokerite Wax 2389 | Ozokerite | | | | | | | 2 | | | | |
| PCL-liquid 100 | Cetearyl Ethylhexanoate | | | 2 | | 4 | 5 | | | | | |
| PCL-Solid | Stearyl Heptanoate, Stearyl Caprylate | | | | | 3 | | | 0.5 | | | |
| Phytoconcentrole ® Coconut | Caprylic/Capric Triglyceride, Coconut (Cococ Nucifera) Oil | | | | | | | | 1 | | | |
| Rewoderm LI S80 | PEG-200 Hydrogenated Palmitate, PEG-7 Glyceryl Cocoate | | | | | | | | | 0.25 | | |
| Rewopol SBFA30 | Disodium Laureth Sulfosuccinate | | | | | | | | | | 8 | |
| Silcare Silicone 41M65 | Stearyl Dimethicone | | | 1 | | | | | 21 | | | |
| Sodium Chloride | Sodium Chloride | | | | | | | | | 1.7 | | |
| Sodium Hydroxide 10% sol. | Sodium Hydroxide | | | | | 0.9 | | | | | | |
| Solubilizer | PEG-40 Hydrogenated Castor Oil, Trideceth-9, Propylene Glycol, Water (Aqua) | | | | | | | 1.5 | | | | 0.5 |
| Sym3D ® | Hydroxymethoxyphenyl Propylmethylmethoxybenzofuran | | | 0.2 | | | | | | | | |
| SymCalmin ® | Pentylene Glycol, Butylene Glycol, Hydroxyphenyl Propamidobenzoic Acid | | | | | 1 | | | | | | |
| SymClariol ® | Decylene Glycol | | | 0.5 | | | | | | | | |
| SymDiol ® 68 | 1,2 Hexanediol, Caprylyl Glycol | 0.6 | | | | | | | 1 | | | |
| SymFinity ® 1298 | *Echinacea Purpurea* Extract | | | 0.5 | | | | | | | | |
| SymFit ® 1617 | Trimethylcyclohexyl Butylcarbamate | | | | | 0.1 | | | | | | |

-continued

| Ingredients | INCI-Name | 9 | 10 | 11 | 12 | 13 | 14 | 15 | 16 | 17 | 18 | 19 |
|---|---|---|---|---|---|---|---|---|---|---|---|---|
| SymFit ® nat 1750 | Propanediol, *Bobgunnia Madagascariensis* Wood Extract | | | | 1 | | | | | | | |
| SymGlucan ® | Water (Aqua) Glycerin, Beta Glucan | | 2 | | 2 | 1 | | 5 | | | | |
| SymHelios ® 1031 | Benzylidene Dimethoxydimethylindanone | | | 0.5 | 0.5 | | | | | | | |
| SymMatrix ® | Maltodextrin, *Rubus Fruticosus* (Blackberry) Leaf Extract | | | | | | 0.5 | | | | | |
| SymMollient ® L | Neopentyl Glycol Diisononanoate | | | | 2 | | | | | | 5 | |
| SymMollient ® S | Cetearyl Nonanoate | | | | 1 | | | | | | 4 | |
| SymMollient ® W/S | Trideceth-9, PEG-5 Isononanoate | | | | | | | 2 | | | | |
| SymOcide ® PS | Phenoxyethanol, Decylene Glycol, 1,2-Hexanediol | | | | | | 0.7 | | | | | |
| SymRelief ® 100 | Bisabolol, *Zingiber Officinale* (Ginger) Root Extract | 0.1 | | 0.1 | | | 0.1 | | 0.1 | | | |
| SymRelief ® S | Bisabolol, Hydroxymethoxyphenyl Decanone | | 0.1 | | 0.1 | 0.2 | | 0.1 | | 0.1 | | |
| SymRepair ® | Hexyldecanol, Bisabolol, Cetylhydroxyproline Palmitamide, Stearic Acid, *Brassica Campestris* | | | 1 | | | 3 | | | | 1 | 0.5 |
| SymSitive ®1609 | Pentylene Glycol, 4-t-Butylcyclohexanol | | | | | 0.5 | | | | | | |
| SymVital ® | *Aloe Barbadensis* Leaf Juice Powder, Magnesium Ascorbyl Phosphate, Rubus Idaeus | 0.5 | | | | | | 0.1 | | | | |
| Tinosorb S | Bis-Ethylhexyl-oxyphenol, Methoxyphenyl Triazine | | | | | | | | | | 3 | |
| Tapioca Pure | Tapioca Starch | | | 5 | | | | | | | | |
| TeCe-Ozokerit N502 | Ozokerite | | | | | | | | | | ad 100 | |
| Tego Betain L7 | Cocoamidopropyl Betaine | | | | | | | | | 5 | | |
| Tegosoft TN | C12-15 Alkyl Benzoate | | | | | 5 | | | | | | |
| Texapon N70 | Sodium Laureth Sulfate | | | | | | | | | 15 | | |
| Triethanolamine 99% | Triethanolamine | | | | | | | | | | | 0.5 |
| Vitamin E acetat | Tocopherol Acetate | | 0.5 | 0.5 | 0.5 | | 0.2 | 0.5 | | 0.7 | | |
| Wacker-Belsil CDM3526 VP | C26-C28 Alkyl Dimethicone | | | | | | | | | | 2 | |
| Water, demin. | Water (Aqua) | ad 100 | ad 100 | ad 100 | ad 100 | ad 100 | ad 100 | ad 100 | | ad 100 | | ad 100 |

The invention claimed is:
1. A skin or hair whitening mixture, consisting of:
about 30 to about 99% of phenylethyl resorcinol
(b) about 1 to 20% of bisabolol; and,
(c) 10 to 50% of alkane diols selected from the group consisting of 1,2-propandiol, 1,3-propandiol, 1,2-butandiol, 1,2-pentandiol, 1,2-hexandiol, 1,2-heptandiol, 1,2-octandiol, 1,2-nonandiol, 1,2-decandiol and their mixtures, on condition that the amounts of (a), (b) and (c) add up to 100% by weight wherein the skin or hair whitening mixture is dissolved in a cosmetically acceptable oil body and wherein the mixture is present in an amount of from about 0.1 to about 10% by weight based on the total weight of the cosmetically acceptable oil body and the mixture.

2. The skin or hair whitening mixture of claim 1, wherein the alkandiol is 1,2-pentandiol.

3. A cosmetic composition comprising the skin or hair whitening mixture of claim 1.

4. The cosmetic composition of claim 3, wherein said cosmetic composition is an anti-ageing face cream, a BB cream, an anti-dark spot cream, a whitening post depilatory cream, a whitening deodorant, a body lotion or a soap and body wash.

5. A non-therapeutic method for whitening human skin or hair, the method comprising topical administration of a working amount of the skin or hair whitening mixture of claim 1.

6. A non-therapeutic method for whitening human skin or hair, the method comprising topical administration of a working amount of the cosmetic composition of claim 3.

* * * * *